(12) United States Patent
Andersen et al.

(10) Patent No.: US 6,861,237 B2
(45) Date of Patent: Mar. 1, 2005

(54) PRODUCTION OF HETEROLOGOUS POLYPEPTIDES IN YEAST

(75) Inventors: Asser Sloth Andersen, Herlev (DK); Ivan Diers, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 212 days.

(21) Appl. No.: 10/002,826

(22) Filed: Nov. 30, 2001

(65) Prior Publication Data

US 2005/0019853 A1 Jan. 27, 2005

Related U.S. Application Data

(60) Provisional application No. 60/256,602, filed on Dec. 19, 2000.

(30) Foreign Application Priority Data

Nov. 30, 2000 (DK) .......................................... 2000 01800

(51) Int. Cl.$^7$ .......................... C12P 21/00; C12P 21/02; C12N 15/81; C12N 15/63
(52) U.S. Cl. .................. 435/69.4; 435/69.1; 435/320.1; 435/243; 435/254.11; 435/254.2; 435/254.1; 536/23.1; 536/23.5; 536/23.51; 536/23.7; 536/24.1
(58) Field of Search .............................. 435/320.1, 69.1, 435/69.4, 243, 254.1, 254.11, 254.2; 536/23.1, 23.5, 23.51, 23.7, 24.1

(56) References Cited

U.S. PATENT DOCUMENTS

| | | | |
|---|---|---|---|
| 4,870,008 A | 9/1989 | Brake | 435/70 |
| 5,618,676 A | 4/1997 | Hitzeman et al. | 435/69.1 |

FOREIGN PATENT DOCUMENTS

| | | |
|---|---|---|
| DE | 195 25 282 A1 | 1/1997 |
| EP | 0 613 529 A1 | 12/1985 |
| WO | WO 98/26079 | 6/1998 |

OTHER PUBLICATIONS

Chevallier et al., Gene, 1980, vol. 11, pp. 11–19.*
Suissa et al., The EMBO Journal, vol. 3, No. 8, pp. 1773–1781 (1984).
Bloxham et al., Mol. Gen. Genct., vol. 191, pp. 499–506 (1983).
Egel–Mitani et al., Gene, vol. 73, pp. 113–120 (1988).
Rosenkrantz et al., Curr Genet, vol. 25, pp. 185–195 (1994).
Rosenkrantz et al., Molecular Microbiology, vol. 13, pp. 119–131 (1994).

* cited by examiner

*Primary Examiner*—David Guzo
(74) *Attorney, Agent, or Firm*—Reza Green; Len Smith; Richard Bork

(57) ABSTRACT

A process for producing high amount of proteins or polypeptides in yeast is disclosed. The process makes use of the CIT1 yeast promoter or a functional part or variant thereof. Examples of polypeptides which are expressed in high yields are insulin or insulin analogues or GLP1.

19 Claims, 2 Drawing Sheets

Fig. 2

```
                            G   GA
         1    TATAAGAGAG CTCATCTTAT TGTTGTCAGC CCAATGATTC CCTTGTCAAA
        51    TTGAATTTTC GGATTTACTT GTTCAGGTAC CCGCGTTAAG GGGCTGCCGC
       101    GCCTGTCACT CTAAGAAAAA AGGAGCCATC AAAAACCATT CAGCATTAAC
       151    TAAAAACGCG GGTAGAGATT ACTACATATT CCAACAAGAC CTTCGCAGGA
       201    AAGTATACCT AAACTAATTA AAGAAATCTC CGAAGTTCGC ATTTCATTGA
       251    ACGGCTCAAT TAATCTTTGT AAATATGAGC GTTTTACGT TCACATTGCC
       301    TTTTTTTTA TGTATTTACC TTGCATTTTT GTGCTAAAAG GCGTCACGTT
       351    TTTTCCGCC GCAGCCGCCC GGAAATGAAA AGTATGACCC CCGCTAGACC
       401    AAAAATACTT TTGTGTTATT GGAGGATCGC AATCCCTTTG GAGCTTTTCC
       451    GATACTATCG ACTTATCCGA CCTCTTGTTG TTTGAAAATG TCAATTGATA
       501    TCCATCCATT ATATAAATGC TCAAAACTTG CAGCAACTAT TCTTTACCCT
       551    TCCCCTGTTA TGGATTGCTA GTCTTAAGGG GGAAATTTGC TGTTTACTAA
       601    AATACAAACC AGGTTTGTTT TGGCTTTTAT TTGCATTTAA GTAATTACAA
       651    TTACAACCAT TAAAAAGAAA ATAAGGCAAA ACATATAGCA ATATAATACT
                           T  TC
       701    ATTTACGAAG ATGTCAGCGA TA
```

SEQUENCE LISTING

<160> NUMBER OF SEQ ID NOS: 7

<210> SEQ ID NO 1
<211> LENGTH: 722
<212> TYPE: DNA
<213> ORGANISM: Saccharomyces cerevisiae

<400> SEQUENCE: 1

```
tataagagag ctcatcttat tgttgtcagc ccaatgattc ccttgtcaaa ttgaattttc      60
ggatttactt gttcaggtac ccgcgttaag gggctgccgc gcctgtcact ctaagaaaaa     120
aggagccatc aaaaaccatt cagcattaac taaaaacgcg ggtagagatt actacatatt     180
ccaacaagac cttcgcagga aagtatacct aaactaatta agaaatctc cgaagttcgc      240
atttcattga acggctcaat taatctttgt aaatatgagc gttttacgt tcacattgcc      300
ttttttttta tgtatttacc ttgcattttt gtgctaaaag gcgtcacgtt tttttccgcc     360
gcagccgccc ggaaatgaaa agtatgaccc ccgctagacc aaaaatactt ttgtgttatt     420
ggaggatcgc aatcccttg gagcttttcc gatactatcg acttatccga cctcttgttg      480
tttgaaaatg tcaattgata tccatccatt atataaatgc tcaaaacttg cagcaactat     540
tctttaccct tcccctgtta tggattgcta gtcttaaggg ggaaatttgc tgtttactaa     600
aatacaaacc aggtttgttt tggctttat ttgcatttaa gtaattacaa ttacaaccat      660
taaaagaaa ataaggcaaa acatatagca atataatact atttacgaag atgtcagcga     720
ta                                                                    722
```

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Glu Glu Ala Glu Ala Glu Ala Lys
 1               5

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3

```
tataagagag gtcgacttat tgttgtcagc ccaatgattc                            40
```

<210> SEQ ID NO 4
<211> LENGTH: 42
<212> TYPE: DNA
<213> ORGANISM: Artificial Sequence
<220> FEATURE:
<223> OTHER INFORMATION: Synthetic

<400> SEQUENCE: 4

```
tatcgctgac gaattcgtaa atagtattat attgctatat gt                         42
```

<210> SEQ ID NO 5
<211> LENGTH: 6
<212> TYPE: PRT

```
-continued

<213> ORGANISM: Artificial Sequence
<220> FEATURE:
<223> OTHER INFORMATION: Synthetic

<400> SEQUENCE: 5

Glu Glu Ala Glu Pro Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Glu Glu Gly Glu Glu Pro Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Glu Glu Ala His Lys
1               5
```

US 6,861,237 B2

PRODUCTION OF HETEROLOGOUS POLYPEPTIDES IN YEAST

CROSS REFERENCE TO RELATED APPLICATIONS

This application claims priority under 35 U.S.C. 119 of Danish application no. PA 2000 01800 filed on Nov. 30, 2000, and U.S. provisional application No. 60/256,602 filed on Dec. 19, 2000, the contents of which are fully incorporated herein by reference.

FIELD OF THE INVENTION

The present invention relates to a method for production of heterologous polypeptides or intermediates thereof in yeast, in particular polypeptides of non-bacterial origin. The invention also relates to DNA sequences and vector constructs for use in such method and transformed yeast cells.

BACKGROUND OF THE INVENTION

Yeast is a widely used organism for production of desired proteins or polypeptides. Expression of foreign proteins or polypeptides in yeast is disclosed in e.g. EP 163,529, U.S. Pat. No. 4,870,008 and U.S. Pat. No. 5,618,676.

For commercial application high yields of the expressed polypeptides is important. A number of different factors will have an impact on the expression yield including the promoter and so-called upstream activating sequences. It is generally accepted that the best result is achieved when a promoter that is homologous to the host organism is used for expression of both native and foreign genes in transformed host cells. Thus for expression of foreign genes in yeast a promoter associated with a yeast gene would be preferred. Several promoters useful for expression of heterologous proteins in yeast are known. The most commonly used yeast promoters include the PGK, TPI, ADH2, PHO5, MFα1 and GAP promoters.

There is, however, a constant need for further promoters that have improved efficiency and the capability of being regulated for use in large scale thus enabling a high level of expression yield in commercial production.

SUMMARY OF THE INVENTION

The present invention provides a process for expression of heterologous non-bacterial polypeptides in yeast wherein a yeast promoter associated with the yeast CIT1 gene or a functional part or variant of the CIT1 promoter is used for expression of the heterologous gene.

In its broadest aspect the present invention is related to a process for making a heterologous, non-bacterial polypeptide in yeast or an intermediate therefore comprising (i) culturing a yeast strain comprising a polynucleotide sequence encoding the desired polypeptide or an intermediate therefore under suitable culture conditions for expression of said polypeptide, wherein the polynucleotide sequence encoding the desired polypeptide or its intermediate is under transcriptional control of a CIT1 yeast promoter or a functional part or variant thereof, and (ii) isolation of the desired poly peptide or its intermediate.

In another aspect the present invention it is related to a polynucleotide construct comprising a polynucleotide sequence encoding a non-bacterial polypeptide or an intermediate therefore and the CIT1 yeast promoter or a functional part or variant of the CIT1 promoter.

In a further aspect, the present invention is related to a vector construct comprising in proper reading frame (a) the yeast CIT1 promoter or a functional part or variant thereof, (b) a polynucleotide sequence encoding a non-bacterial polypeptide or an intermediate therefore, (c) a suitable leader sequences and (d) possible a transcription terminator sequence.

In a further aspect, the present invention is related to yeast cells being transformed with the polynucleotide construct or vector of the invention.

The yeast promoter CIT1 directs the expression of the yeast citrate synthase gene CIT, vide Rosenkrantz et al, Curr Genet (1994) 25:185–195 and Rosenkrantz et al Molecular Microbiology (1994) 13(1), 119–131. The CIT1 promoter sequence is comprised in the sequence complementary to the sequence from position 2434 to position 3155 of GenBank accession number Z71616.

In another embodiment of the present invention the CIT1 promoter sequence is contained in SEQ ID NO:1 and will typically consist of all or part of the nucleotide sequence of SEQ ID NO:1. The promoter sequence used in the present invention may furthermore consist of all or part of the nucleotide sequence from 10 to 722 of SEQ ID NO:1. In a further embodiment the promoter will consist of all or part of the nucleotide sequence from position 150 to 722 of SEQ ID NO:1 and in a still further embodiment the promoter may consist of all or part of the nucleotide sequence from position 150 to 530 of SEQ ID NO:1.

BRIEF DESCRIPTION OF THE DRAWINGS

FIG. 2 shows the 722 nucleotide DNA sequence (SEQ ID NO:1) containing the CIT1 promoter described in example 1. Above the sequence is shown the nucleotide changes introduced by oligonucleotides E102 and E103. The underlined sequences denote the restriction sites introduced by these changes. The nucleotide sequence corresponds to the complementary sequence from position 2434 to position 3155 of GenBank accession number Z71616.

DETAILED DESCRIPTION

Figure 1:
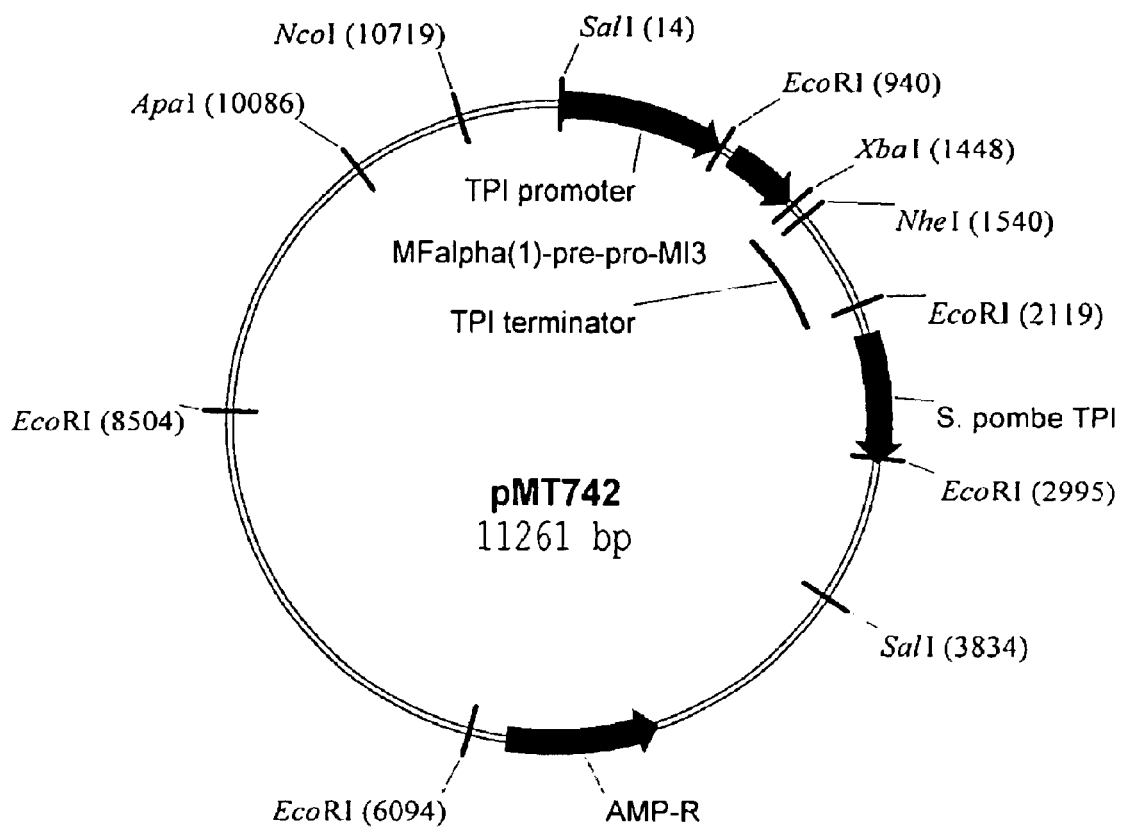
FIG. 1 shows an example of a yeast plasmid called pMT742 (Egel-Mitani et al., Gene, 73, 1988, 99. 113–120). The plasmid contains an expression cassette comprising an EcoRI -XbaI fragment inserted into the plasmid between the transcription-promoter (located on a Sa/I—EcoRI fragment) and the transcription-terminator of the S. cerevisiae TPI gene.

With "CIT1" yeast promoter is meant the natural or wild type yeast promoter sequence disclosed by Rosenkrantz et al, Curr Genet (1994) 25:185–195) and Rosenkrantz et al, Molecular Microbiology (1994) 13(1): 119–131) or its complementary sequence. It is well known in the art that not all part of a natural promoter sequence is necessary for efficient transcription. Resections may be made at the N-terminal end or at the C-terminal end or at both the N-terminal and C-terminal ends. Furthermore one or more nucleotides can be deleted within the promoter sequence. Also, a minor number of individual nucleotides may be changes to other nucleotides, e.g. to introduce a suitable restriction site. Thus "a functional part or variant of the CIT1 promoter" in this context is intended to cover such modified forms of the natural CIT1 promoter sequence as long as the transcriptional promoter activity is not adversely affected. A retention of at least 75% of the transcriptional promoter activity compared to a similar construct where everything else is the same except for the promoter sequence will be preferred. The functional part or variant of the CIT1 promoter should not have less than 65% and more typically not less than at least 70 to 95% of the transcriptional promoter activity of the unchanged promoter.

In the context of the present invention a variant of the CIT1 promoter will include any sequence obtained from the SEQ ID NO:1 by mutation, deletion, substitution, addition and/or modifications of one or more nucleotides as long as the promoter variant retains at least 65% of its transcriptional promoter activity in the unmodified state.

Whether a functional part or variant of the CIT1 promoter has retained at least 65% of its transcriptional promoter activity in the unchanged form can be demonstrated in various ways for example by use of a reporter gene which's expression is detectable in a convenient way. The promoter and its variants may be preceded by upstream activating sequences "UAS" as well known in the art.

A coding sequence is under "transcriptional control" of a promoter when RNA polymerase binds to the transcription initiation sequence and transcribes the coding sequence into mRNA terminating at the transcription termination sequence and the mRNA is then translated into the polypeptide encoded by the coding sequence.

By "in proper reading frame" is meant that the individual polynucleotide sequences are operably connected in such a way that the coding sequence is under the transcriptional control of the yeast recognized promoter and terminator sequences.

By "yeast-recognized" promoter and terminator sequences is meant regulatory sequences that are functional in yeast.

By "percent sequence identity" is meant percent identity between two nucleotide sequences when aligned and compared nucleotide to nucleotide. Methods for sequence alignment and for determination of the percent identity are well known in the art, see for example Smith T. F. and Waterman M. S. (1981) Identification of common molecular subsequences. J. Mol. Biol. 147:195–7.

"POT" is the *Schizosaccharomyces pombe* triose phosphate isomerase gene, and "TPI1" is the *S. cerevisiae* triose phosphate isomerase gene.

By "insulin precursor" is meant a single-chain polypeptide which by one or more subsequent chemical and/or enzymatic processes can be converted to a two-chain human insulin. The single-chain insulin precursor will contain correctly positioned disulphide bridges (three) as in human insulin.

By a "leader" is meant an amino acid sequence consisting of a pre-peptide (the signal peptide) and a pro-peptide.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast c-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98132867. The pro-peptide will preferably contain an endopeptidase processing site at the C-terminal end, such as a Lys-Arg sequence or any functional analogue thereof.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally deaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analogue (Egel-Mitani et al. (1990) YEAST 6:127–137) and the α-factor product of the MFα1 gene (Thorner (1981) in *The, Molecular Biology of the Yeast Saccharomyces cerevisise*, Strathem et al., eds., pp 143–180, Cold Spring Harbor Laboratory, N.Y.).

As used herein "a heterologous protein or polypeptide" is one in which the mature part of the protein sequence (i.e., other than the signal peptide, leader peptide, spacer peptide, and the like) is derived from a different species than that of the host cell. Preferably, the heterologous protein or polypeptide is a non-bacterial protein or polypeptide. With "a non-bacterial protein or polypeptide" is meant a protein or polypeptide not derived from a bacterial cell.

In one series of embodiments, the heterologous polypeptide is an insulin precursor or an insulin precursor-analogue. An insulin precursor or insulin precursor analogue is a single-chain polypeptide that can be converted into insulin or an insulin analogue by one or more subsequent chemical and/or enzymatic processes. The insulin includes, without limitation, human insulin. An insulin analogue has one or more mutations, substitutions, deletions and or additions of the A and/or B amino acid chains relative to the native insulin sequence. Preferably, the insulin analogues contain deletions or substitutions of one, two, or three amino acids.

"DesB30" or "B(1–29)" refers to a human insulin B chain sequence lacking the B30 amino acid residue. "A(1–21)" refers to a native human insulin A chain. "MI3" refers to a single chain insulin precursor in which B(1–29) is linked to A(1–21) via a short peptide bridge (AlaAlaLys).

In another embodiment the heterologous polypeptide is GLP-1. The amino acid sequence of GLP-1 is given i.a. by Schmidt et al. (*Diabetologia* 28 704–707 (1985). GLP-1 (7–37) and analogues thereof have attracted much attention in recent years. Other examples of a heterologous polypeptides are GLP-2 and glucagon both belonging to the GRF (growth hormone releasing factor) family of peptides having a His or Tyr in the N-terminal position and Ser, Ala or Gly in the next position, vide Adelhorts K. et al., The Journal of Biological Chemistry (1994) p 6275–6278).

By "an intermediate" is meant a polypeptide or protein which can be converted into the desired final product by suitable chemical or physical means.

By "connecting peptide" or "C-peptide" is meant the connection moiety of the B-C-A polypeptide sequence of a single chain preproinsulin-like molecule. Specifically, in the natural insulin chain, the C-peptide connects position 30 of the B chain and position 1 of the A chain.

The polynucleotide sequence of the invention may be prepared synthetically by established standard methods, e.g. the phosphoamidite method described by Beaucage et al. (1981) Tetrahedron Letters 22:1859–1869, or the method described by Matthes et al. (1984) EMBO Journal 3:801–805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in yeast and which carries a polynucleotide sequence encoding the desired polypeptide. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Examples of sequences: which enable the vector to replicate in yeast are the yeast plasmid 2 $\mu$m replication genes REP 1–3 and origin of replication.

Alternatively, the vector may be one which, when introduced into the host cell, is intergrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtiiis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125–130).

In the vector, the polynucleotide sequence is operably connected to the promoter sequence of the invention. The promoter sequence may be preceded by up stream enhancer sequences.

The invention encompasses a recombinant expression vector which is capable of replicating in yeast and which carries a polynucleotide construct encoding the desired product or an intermediate therefore. The recombinant expression vector may be any vector which is capable of replicating in yeast organisms. In the vector, the polynucleotide sequence should be operably connected to the selected promoter sequence. The polynucleotide construct of the invention may also be operably connected to a suitable terminator, for example the TPI terminator (Alber et al. (1982) J. Mol. Appl. Genet. 1:419–434).

The procedures used to ligate the polynucleotide constructs of the invention, the promoter and the terminator, respectively, and to insert them into suitable yeast vectors containing the information necessary for yeast replication, are well known to persons skilled in the art. It will be understood that the vector may be constructed either by first preparing a DNA construct containing the entire DNA sequence of the invention, and subsequently inserting this fragment into a suitable expression vector, or by sequentially inserting DNA fragments containing genetic information for the individual elements (such as the signal, leader, promoter and the desired product) followed by ligation.

The yeast organism used in the process of the invention may be any suitable yeast organism which, on cultivation, produces large amounts of the insulin precursor and insulin precursor analogues of the invention. Examples of suitable yeast organisms may be strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida*sp., *Candida utilis, Candida cacaoi, Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms in industrial scale. The design and operation of a typical fermentor is described in Bailey & Ollis, Biochemical Engineering Fundamentals, p620–26, Sec.ed. 1986, McGraw-Hill, ISBN 0-07-003212-2A. The cultivation may be conducted as a batch culture, i.e. all ingredients added before inoculation, as a fed batch culture where a limiting nutrient is added during the fermentation or as a continuous culture which means that at a constant feed of complete, medium is fed to the fermentor and an equal amount of culture medium is removed from the fermentor as described in Aiba, Humphey and Millis: Biochemical Engineering, Academic Press. N.Y., 1965. In one embodiment the cultivation is conducted as a batch culture that is a closed culture system which contains, an initial, limited amount of nutrients.

With "industrial or commercial scale" is meant production scale higher than 10 m$^3$, preferably between 10 and 500 m$^3$, more preferably between 50 and 200 m$^3$ and even more preferably between 80 and 180 m$^3$.

The expressed product will be recovered from the medium by conventional procedures including separating the yeast cells from the medium by centrifugation or filtration, precipitating the proteinaceous components of the supernatant or filtrate by means of a salt, e.g. ammonium sulphate or by ion exchange chromatography, followed by purification by a variety of chromatographic procedures, e.g. ion exchange chromatography, affinity chromatography, or the like.

After secretion to the culture medium and recovery, the isolated polypeptide may be subjected to various in vitro procedures for example to remove a possible N-terminal extension sequence and/or other unwanted sequences in the expressed and secreted product. Thus the desired polypeptides, e.g. an insulin precursor or an insulin precursor analogue may be expressed with an N-terminal amino acid residue extension, as described in U.S. Pat. No. 5,395, 922, and European Patent No. 765,395A, both of which patents are herein specifically incorporated by reference. The N-terminal extension may be removed from the recovered insulin precursor or insulin precursor analogue by means of a proteolytic enzyme which is specific for a basic amino acid (e.g., Lys) so that the terminal extension is cleaved off at the Lys residue. Examples of such proteolytic enzymes are trypsin or *Achromobacter lyticus* protease. If the insulin precursor or insulin precursor analogue comprise a connecting peptide such connecting peptide will cleaved off by in vitro enzymatic conversion by means of trypsin or a trypsin like enzyme or an *Achromobacter lyticus* protease. If the insulin precursor or insulin precursor analogue is expressed and secreted as single chain precursor wherein the B29 amino acid residue is linked to the A1 amino acid residue by means of a peptide bond or a connecting peptide such as an AlaAlaLys sequence (MI3) the insulin precursor is converted into insulin by enzymatic conversion with trypsin or *Achromobactor lyticus* protease in the presence of an L-threonine ester followed by conversion of the threonine ester of the insulin or insulin analogue into insulin or the insulin analogue by basic or acid hydrolysis as described in US patent specification No. U.S. Pat. No. 4,343,898 or U.S. Pat. No. 4,916.212.

The present invention is described in further detail in the following examples that are not in any way intended to limit the scope of the invention as claimed. The attached Figures are meant to be considered as integral parts of the specification and description of the invention. All references cited are herein specifically incorporated by reference for all that is described therein.

EXAMPLES

General Procedures:
Plasmids and DNA

All expressions plasmids are of the C-POT type, similar to those described in WO EP 171 142, which are characterized by containing the *Schizosaccharomyces pombe* triose phosphate isomerase gene (POT) for the purpose of plasmid selection and stabilization in *S. cerevisiae*. The plasmids furthermore contain the *S. cerevisiae* triose phosphate isomerase terminator.

Yeast Strain and Transformation

*S. cerevisiae* strain MT663 (MATaIMATαpep4-3/pep4-3 HIS4/his4 tpi::LEU2/tpi::LEU2 Cir⁺) or *S. cerevisiae* strain ME1719 (MATa/MATαΔyap3::URA3/Δyap3::ura3 pep4-3/pep4-3 Δtpi::LEU2Δtpi::LEU2 leu2/leu2 URA3/URA3) were used as host strains for transformation. Strain MT663 was deposited in the Deutsche Sammlung von Mikroorganismen und Zellkulturen in connection with filing WO 92/11378 and was given the deposit number DSM 6278. Strain ME1719 is described in WO 98/01535. Transformation of MT633 and MT1719 was; conducted as described in WO 97/22706 and WO 98/01535, respectively.

Yeast Expression

Yeast strains harbouring plasmids as described above, were grown in YPD media (Guthrie, C. & Fink, G.R., Eds., Guide to Yeast Genetics and Molecular Biology, Academic Press, 1991). For each strain 2–4 individual 5 ml cultures were shaken at 30° C. for 72 hours, with a final $OD_{600}$ of approximately 15–20. After centrifugation the supernatant was removed for quantitative analysis by which method the concentration of secreted heterologous product was measured. For GLP-1 the analysis was by HPLC as described in copending patent application DK PA 2001 01141. For insulin precursors the analysis was by HPLC by a method described by Snel, L. et al. *Chromatographia* 24 (1987) 329–332. For Sf-IBP an insulin binding assay was performed as described by Andersen, A. S. et al., *J. Biol. Chem.* 275 (2000) 16948–16953. For AMMEP an assay for proteolytical activity was performed as follows: An MI3 precursor with the extension GluGluAlaGluAlaGluAlaLys (SEQ ID NO:2) (described in Kjeldsen et al., Gene 170: 107–112, 1996) was incubated with supernatant from yKV333 or yEA284 overnight at 37° C. Subsequently the supernatants were analysed for GluGluAlaGluAlaGluAlaLys(SEQ ID NO:2)-extended MI3 or MI3 with a single N-teminal Lys residue (the product that results from AMMEP cleavage) by HPLC as described above. The ratio of Lys-MI3/GluGluAlaGluAlaGluAlaLys (SEQ ID NO:2)-MI3 was used as a measure for AMMEP expression level.

In Table 1 the expression levels of a number of insulin precursors, a GLP-1(7–37)Lys34Arg analogue as well as Sf-IBP and AMMEP obtained by use of the CIT1 promoter are given as percentage of the level obtained with the corresponding constructs using the TPI1 promoter in stead of the CIT1 promoter.

Example 1

Construction of Expression Vector Encoding an Insulin Precursor M13 Under Expression Control of the CIT1 Promoter FIG. 1 shows a yeast plasmid called pMT742 (Egel-Mitani et al., Gene, 73, 1988, 99. 113–120). The plasmid contains an expression cassette comprising an EcoRI-XbaI fragment inserted into the plasmid between the transcription-promoter (located on a SalI-EcoRI fragment) and the transcription-terminator of the *S. cerevisiae* TPI gene.

In plasmid pMT742 the EcoRI-XbaI fragment encodes a fusion product composed of the MFα1 pre-pro leader, a Lys-Arg cleavage site for the dibasic processing endopeptidase KEX2, and the single-chain mini-insulin precursor MI3. In order to construct a plasmid where the promoter from the TPI gene has been replaced by the promoter from the CIT1 gene of *S. cerevisiae*, the following steps were performed using standard molecular biology techniques (e.g. Sambrook, J., Fritsch, E.F. and Maniatis, T., Molecular Cloning: A laboratory Manual, Cold Spring Harbour Laboratory Press, New York, 1989).

A 722 bp DNA fragment containing the CIT1 promoter was amplified with PCR from genomic *S. cerevisiae* DNA (from strain MT663) using oligonucleotides E102 (5'-TAT AAG AGA GGT CGA CTT ATT GTT GTC AGC CCA ATG ATT C-3') (SEQ ID No: 3) and E103 (5'-TAT CGC TGA CGA ATT CGT AAA TAG TAT TAT ATT GCT ATA TGT-3') (SEQ ID No:4). E102 has been designed to introduce a SaiI restriction site, and E103 an EcoRI restriction site, into the amplified DNA fragment. After digestion with SalI and EcoRI the CIT1 promoter can thus be cloned as a SalI-EcoRI fragment.

To facilitate the cloning, the ApaI-EcoRI of pMT742 containing the TPI promoter from *S. cerevisiae* was subcloned into a pBluescriptII-SK (Stratagene) ApaI-EcoRI vector fragment. The resulting plasmid pEA222 was digested with SalI and EcoRI and the vector fragment was ligated to the SalI/EcoRI DNA fragment containing the CIT1 promoter. The resulting plasmid pSurf/CIT was digested with NcoI and EcoRI and the DNA fragment containing the CIT1 promoter was ligated to the NcoI/XbaI vector fragment and the EcoRI/XbaI fragment from pMT742 resulting in the final plasmid pEA268.

The expression plasmid was propagated in *E. coli*, grown in the presence of ampicillin and isolated using standard techniques (Sambrook et al., 1989). The plasmid DNA was checked for insert by appropriate restriction nucleases (e.g. EcoRI, NcoI, SalI, XbaI) and was shown by sequence analysis to contain the proper sequence of the CIT1 promoter.

The plasmid pEA268 was transformed into *S. cerevisiae* strain MT663. Yeast transformants harbouring plasmid pEA268 were selected by glucose utilization as carbon source on YPD (1% yeast extract, 2% peptone, 2% glucose) agar (2%) plates and the resulting strain was named yEA268. The control strain MT742 is MT633 transformed with pMT742.

Example 2
Construction of Expression Vector Encodino an N-terminal Extended Insulin Precursor M13 Under Expression Control of the CIT1 Promoter.

The EcoRI/XbaI DNA fragment containing the expression cassette from plasmid pAK729 (described in WO 97/22706) encodes a fusion product composed of a signal peptide followed by a synthetic leader, a Lys-Arg cleavage site for the dibasic processing endopeptidase KEX2, a spacer and processing site (GluGluAlaGluProLys) (SEQ ID NO:5) and the single-chain mini-insulin precursor MI3. This fragment was ligated to the NcoI/XbaI and the NcoI/EcoRI fragment (containing the CIT1 promoter) from pEA268 resulting in the final plasmid pEA274. The plasmids were propagated in E. coli, isolated and checked for the correct insert as in example 1. The plasmids pAK729 and pEA274 were transformed into S. cerevisiae strain MT663 and transformants selected as described in example 1. The resulting yeast strains were named yAK729 and yEA274, respectively.

Example 3
Construction of Expression Vector Encoding an N-Terminal Extended Insulin Precursor (B(1–29)Asp-Pro-Lys-A(1–21)) Under Expression Control of the CIT1 Promoter.

Copending patent application DK PA 2001 00547 discloses expression of a fusion product comprising a signal peptide followed by a synthetic leader, a LysArg cleavage site for the dibasic processing endopeptidase KEX2, a spacer and processing site (GluGluGlyGluGluProLys) (SEQ ID NO:6) and an insulin precursor B(1–29)-AspProLys-A(1–21). An EcoRI/XbaI fragment containing DNA encoding this fusion product was ligated to the NcoI/XbaI and the NcoI/EcoRI fragment (containing the CIT1 promoter) from pEA268. The resulting plasmids were propagated in E. coli, isolated and checked for the correct insert as in example 1 and were transformed into S. cerevisiae strain ME1719. Transformants were selected as described in example 1. Yields compared to the control are given in Table 1.

Example 4
Expression of GLP-1(7–37)Arg34 with an N-terminal Extension

Copending patent application DK PA 2001 01141 discloses expression of a fusion product comprising the MFα1 pre-pro leader, a LysArg cleavage site for the dibasic processing endopeptidase KEX2, a spacer and processing site GluGluAlaHisLys (SEQ ID NO: 7) and a GLP-1 analogue wherein Lys in position 34 is substituted with an Arg. An EcoRI/XbaI DNA fragment containing the DNA encoding the fusion product was ligated to the ApaI/XbaI and the ApaI/EcoRI fragment (containing the CIT1 promoter) from pEA268. The resulting plasmids were propagated in E. coli, isolated and checked for the correct insert as in example 1 and were transformed into S. cerevisiae strain ME1719. Transformants were selected as described in example 1.

Example 5
Construction of Expression Vectors for Sf-IBP containing the TPI or CIT1 Promoter Spodoptera frugipera (fall armyworm) insulin-like peptide binding protein has been described by Andersen, A. S. et al., J. Biol. Chem. 275 (2000) 16948–16953 and the DNA sequence for the gene has been deposited in GenBank with accession number AF236641.

Oligonucleotides were designed that allowed PCR amplification of a DNA fragment according amino acids 23 to 265 of Sf-IBP furnished with an N-terminal extension having the amino acid sequence EEAEPK SEQ ID NO. 5. Using a combination of PCR and overlap PCR, followed by isolation and cloning by standard methods (Horton et al., Gene 77:61–68, 1989, Sambrook et al., 1989) an expression vector pEA263 containing an expression cassette encoding SP-leader-KR-ExtSf-IBP was obtained. The EcoRI/NheI fragment from plasmid pEA263 containing the expression cassette was ligated to the NcoI/NheI and the NcoI/EcoRI fragment (containing the CIT1 promoter) from pEA68 resulting in the final asmid pEA286.

The plasmids were propagated in E. coli, isolated and checked for correct insert as in example 1. Plasmids pEA263 and pEA286 were transformed into S. cerevisiae strain MT663 and transformants were selected as described in example 1. The resulting yeast strains were named yEA263 and yEA286, respectively.

Example 6
Construction of Expression Vector for AMMEP

The gene for the Armillaria mellea endometallopreptidase has been cloned by Vad, K and Thim, L. and the nucleotide sequence has been deposited in GenBank with accession number AJ238718. Oligonucleotides containing EcoRI and XbaI restriction sites were designed to PCR-amplify the entire coding sequence. After isolation and digestion with EcoRI and XbaI, the EcoRI/XbaI DNA fragment containing the entire AMMEP coding sequence was ligated to the NcoI/XbaI vector fragment and the NcoI/EcoRI fragment containing the TPI promoter (both from pMT742) resulting in the final plasmid pKV333.

The EcoRI/XbaI fragment from plasmid pKV333 containing the expression cassette for AMMEP was ligated to the NcoI/XbaI and the NcoI/EcoRI fragment (containing the CIT1 promoter) from pEA268 resulting in the final plasmid pEA284.

The plasmids were propagated in E. coli, isolated and checked for insert as in example 1. Plasmids pKV333 and pEA284 were transformed into S. cerevisiae strain MT663 and transformants selected as in example 1. The resulting yeast strains were named yKV333 and yEA84, respectively.

Table 1 shows the increase in yield by use of the CIT1 promoter compared to the TPI promoter. It appears from the table that use of the CIT1 promoter gives from 50 to more tan 340% increase in expressed and secreted product.

TABLE 1

| Heterologous Product | Relative expression level compared to control |
|---|---|
| MI3 | 142% |
| MI3 with N-terminal extension SEQ ID NO:5 | 180% |
| Sf-IBP | 226% |
| AMMEP | 190% |
| B(1-29)-AspProLys-A(1-21) with N-terminal extension SEQ ID NO:6 | 340% |
| GLP-1(7-37)Arg 34 with N-terminal extension SEQ ID NO:7 | 207% |

What we claim is:

1. A process for making a heterologous, non-bacterial polypeptide or an intermediate therefore in yeast comprising (i) culturing a yeast strain comprising a polynucleotide sequence encoding the polypeptide or an intermediate therefore under suitable culture conditions for expression of the polypeptide or its intermediate, wherein the polynucleotide sequence encoding the polypeptide or its intermediate is expressed under transcriptional control of a yeast CIT1 promoter or a functional part or variant thereof; and (ii) isolating the expressed product.

2. A process according to claim 1, wherein the CIT1 promoter consists of all or part of the nucleotide sequence of SEQ ID NO:1.

3. A process according to claim 1, wherein the CIT1 promoter consists of all or part of the nucleotide sequence from 10 to 722 of SEQ ID NO:1.

4. A process according to claim 1, wherein the CIT1 promoter consists of all or part of the nucleotide sequence from position 150 to 722 of SEQ ID NO:1.

5. A process according to claim 1 wherein the promoter consists of all or part of the nucleotide sequence from position 150 to 530 of SEQ ID NO:1.

6. A process according to claim 1, wherein the expressed product is isolated from the culture medium.

7. A process according to claim 1, wherein the heterologous polypeptide is an insulin precursor.

8. A process according to claim 1, wherein the heterologous polypeptide is GLP-1(7–37).

9. A process according to claim 1, wherein the heterologous polypeptide is GLP-1(7–37)Arg34.

10. A process according to claim 1 being a batch process.

11. A polynucleotide construct comprising a polynucleotide sequence encoding a non-bacterial polypeptide or an intermediate therefore operably linked to a DNA sequence encoding a CITI yeast promoter or a functional part or variant thereof, wherein said polypeptide is heterologous with respect to the CIT1 promoter.

12. A polynucleotide construct according to claim 11, wherein the promoter consists of all or part of the nucleotide sequence of SEQ ID NO:1.

13. A polynucleotide construct according to claim 11, wherein the promoter consists of all or part of the nucleotide sequence from 10 to 722 of SEQ ID NO:1.

14. A polynucleotide construct according to claim 11, wherein the promoter consists of all or part of the nucleotide sequence from position 150 to 722 of SEQ ID NO:1.

15. A polynucleotide construct according to claim 11, wherein the promoter consists of all or part of the nucleotide sequence from position 150 to 530 of SEQ ID NO:1.

16. A polynucleotide construct according to claim 1 further comprising a leader sequence for secretion of the polypeptide.

17. A yeast cell transformed with a polynucleotide construct according to claim 11.

18. A yeast expression vector comprising in proper reading frame (a) a polynucleotide sequence comprising a CIT1 yeast promoter or a functional part or variant thereof, (b) a polynucleotide sequence encoding a non-bacterial heterologous polypeptide or an intermediate therefore, (c) a suitable leader sequence and, optionally (d) a transcription terminator sequence.

19. A yeast cell transformed with a vector according to claim 18.

* * * * *